United States Patent
Shipp (10) Patent No.: US 8,114,099 B2
(45) Date of Patent: Feb. 14, 2012

(54) ABSORBABLE ANCHOR FOR HERNIA MESH FIXATION

(75) Inventor: John I. Shipp, Ponte Vedra Beach, FL (US)

(73) Assignee: Tyco Healthcare Group LP, Mansfield, MA (US)

( * ) Notice: Subject to any disclaimer, the term of this patent is extended or adjusted under 35 U.S.C. 154(b) by 1016 days.

(21) Appl. No.: 10/907,834

(22) Filed: Apr. 18, 2005

(65) Prior Publication Data

US 2006/0129154 A1     Jun. 15, 2006

Related U.S. Application Data

(63) Continuation-in-part of application No. 10/905,020, filed on Dec. 10, 2004, now abandoned, and a continuation-in-part of application No. 10/709,297, filed on Apr. 27, 2004, now Pat. No. 7,758,612.

(51) Int. Cl.
*A61B 17/08* (2006.01)

(52) U.S. Cl. .......................... 606/151; 606/213; 606/304

(58) Field of Classification Search .................. 606/284, 606/298, 295, 301, 305, 312, 316, 317, 151, 606/213, 157, 158, 323, 327; 411/412, 413, 411/386, 398; 29/525
See application file for complete search history.

(56) References Cited

U.S. PATENT DOCUMENTS

| | | | |
|---|---|---|---|
| 1,114,135 A * | 10/1914 | Hafertep | 411/411 |
| RE28,932 E | 8/1976 | Noiles et al. | |
| 4,204,541 A | 5/1980 | Kapitanov | |
| 4,756,653 A * | 7/1988 | Berger | 411/411 |
| 4,824,865 A | 4/1989 | Bowser et al. | |
| 4,895,148 A | 1/1990 | Bays et al. | |
| 4,976,715 A | 12/1990 | Bays et al. | |
| 5,059,206 A | 10/1991 | Womters | |
| 5,080,665 A * | 1/1992 | Jarrett et al. | 606/219 |
| 5,129,906 A * | 7/1992 | Ross et al. | 606/77 |
| 5,163,343 A | 11/1992 | Gish | |
| 5,169,400 A | 12/1992 | Mühling et al. | |
| 5,259,398 A | 11/1993 | Vrespa | |
| 5,354,292 A | 10/1994 | Braeuer et al. | |
| 5,364,400 A * | 11/1994 | Rego et al. | 606/304 |
| 5,582,616 A | 12/1996 | Bolduc et al. | |
| 5,643,320 A | 7/1997 | Lower et al. | |
| 5,730,744 A | 3/1998 | Justin et al. | |
| 5,810,882 A | 9/1998 | Bolduc et al. | |
| 5,824,008 A | 10/1998 | Bolduc et al. | |
| 5,830,221 A | 11/1998 | Stein et al. | |
| 5,891,146 A | 4/1999 | Simon et al. | |
| 5,954,722 A | 9/1999 | Bono | |

(Continued)

FOREIGN PATENT DOCUMENTS

EP     0 121 362     10/1984

(Continued)

OTHER PUBLICATIONS

International Search Report from European Application No. EP 04 75 5078 mailed Jul. 2, 2008.

(Continued)

*Primary Examiner* — Tuan Nguyen (57) ABSTRACT

A method of forming and deploying an improved absorbable anchor for hernia mesh fixation is disclosed. The absorbable anchor of the present invention functions to securely fasten tough, non macro-porous, and relative inelastic mesh to soft tissue. The anchor is formed from co-polymers of lactide and glycolide.

7 Claims, 3 Drawing Sheets

U.S. PATENT DOCUMENTS

| | | |
|---|---|---|
| 5,964,772 A | 10/1999 | Bolduc et al. |
| 5,971,985 A | 10/1999 | Carchidi et al. |
| 6,030,162 A | 2/2000 | Huebner |
| 6,096,060 A | 8/2000 | Fitts et al. |
| 6,296,656 B1 | 10/2001 | Bolduc et al. |
| 6,306,140 B1 | 10/2001 | Dissiqui |
| 6,319,270 B1 | 11/2001 | Grafton |
| 6,533,454 B1 | 3/2003 | Kaikkonen et al. |
| 6,562,051 B1 | 5/2003 | Bolduc et al. |
| 6,747,121 B2 | 6/2004 | Gogolewski |
| 6,884,248 B2 | 4/2005 | Bolduc et al. |
| 6,955,677 B2 | 10/2005 | Dahners |
| 2001/0004694 A1 | 6/2001 | Carchidi |
| 2001/0007074 A1 | 7/2001 | Strobel et al. |
| 2002/0004660 A1 | 1/2002 | Henniges et al. |
| 2002/0013605 A1 | 1/2002 | Bolduc et al. |
| 2003/0036755 A1 | 2/2003 | Ginn |
| 2003/0099102 A1 | 5/2003 | Duval |
| 2003/0135226 A1 | 7/2003 | Bolduc et al. |
| 2004/0073218 A1 | 4/2004 | Dahners |
| 2004/0098045 A1 | 5/2004 | Grafton et al. |
| 2004/0153101 A1 | 8/2004 | Bolduc et al. |
| 2004/0204723 A1 | 10/2004 | Kayan |
| 2004/0254608 A1 | 12/2004 | Huitema et al. |
| 2005/0136764 A1 | 6/2005 | Sherman |
| 2005/0171562 A1 | 8/2005 | Criscuolo et al. |
| 2005/0267478 A1 | 12/2005 | Corradi et al. |
| 2006/0124688 A1 | 6/2006 | Racenet et al. |
| 2006/0273135 A1 | 12/2006 | Beetel |
| 2006/0291981 A1 | 12/2006 | Viola et al. |
| 2008/0097523 A1 | 4/2008 | Bolduc et al. |

FOREIGN PATENT DOCUMENTS

| | | |
|---|---|---|
| EP | 1025803 | 8/2000 |
| EP | 1293168 | 3/2003 |
| EP | 2005975 A2 | 12/2008 |
| FR | 2 299 548 | 8/1976 |
| FR | 2 377 796 | 8/1978 |
| JP | 09149906 | 6/1997 |
| WO | WO 01/62136 | 8/2001 |
| WO | WO 01/97677 | 12/2001 |
| WO | WO 02/30296 | 4/2002 |
| WO | WO 02/091932 | 11/2002 |
| WO | WO 03/034925 | 5/2003 |
| WO | WO 03/049906 | 6/2003 |
| WO | WO 03/103507 | 12/2003 |

OTHER PUBLICATIONS

International Search Report from European Application No. EP 08 02 1125 mailed Mar. 9, 2009.

* cited by examiner

FIG. 7

ABSORBABLE ANCHOR FOR HERNIA MESH FIXATION

The present application is a Continuation-in-Part Application claiming the benefit of and priority to U.S. patent application Ser. No. 10/709,297, filed on Apr. 27, 2004 (now U.S. Pat. No. 7,758,612). the entire contents of which are hereby incorporated by reference.

The present application is a Continuation-in-Part Application claiming the benefit of and priority to U.S. patent application Ser. No. 10/905,020, filed on Dec. 10, 2004 (now abandoned), the entire contents of which are hereby incorporated by reference.

BACKGROUND OF THE INVENTION

This invention relates to surgical fasteners and their associated applicators, and more particularly, surgically fastening material to tissue and their method of use.

In laparoscopic repair of hernias surgical fasteners have been used to attach repair mesh over the hernia defect so that bowel and other abdominal tissue are blocked from forming an external bulge that is typical of abdominal hernias. The role of the fasteners is to keep the mesh in proper position until tissue ingrowth is adequate to hold the mesh in place under various internal and external conditions. Adequate ingrowth usually takes place in 6-8 weeks. After that time the fasteners play no therapeutic role. Fixation anchors comprise a mesh fixation feature, or head, a mesh-tissue interface section, and a tissue-snaring feature that holds the anchor in place under force developed inside or outside the body.

At present, there are a variety of surgical devices and fasteners available for the surgeon to use in endoscopic and open procedures to attach the mesh patch to the inguinal floor or abdominal wall. One such mesh attachment instrument uses a helical wire fastener formed in the shape of a helical compression spring. Multiple helical wire fasteners are stored serially within the 5 mm shaft, and are screwed or rotated into the mesh and the overlaid tissue to form the anchor for the prosthesis. A load spring is used to bias or feed the plurality of helical fasteners distally within the shaft. A protrusion extends into the shaft, while preventing the ejection of the stack of fasteners by the load spring, allows passage of the rotating fastener. U.S. Pat. Nos. 5,582,616 and 5,810,882 by Lee Bolduc, and U.S. Pat. No. 5,830,221 by Jeffrey Stein describe instruments and fasteners of this type.

U.S. Pat. Nos. 5,203,864 and 5,290,297 by Phillips describe two embodiments of a hernia fastener and delivery devices. One of the Phillips fasteners is formed in the shape of a unidirectional dart with flexible anchor members. The dart is forced through the mesh and into tissue by a drive rod urged distally by the surgeon's thumb. The anchor members are forced inward until the distal end of the dart penetrates the overlaid tissue and then the anchor members, presumably, expand outward without any proximal force on the dart thus forming an anchor arrangement. This requires an extremely forceful spring force generated by the anchor members. Multiple darts are stored in a rotating cylinder, much like a revolver handgun.

Phillips second fastener embodiment is a flexible H shaped device. The tissue penetrating means is a hollow needle containing one of the legs of the H. The H shape is flattened with the cross member and the other leg remaining outside the hollow needle owing to a longitudinal slot therein. A drive rod urged distally by the surgeon's thumb again delivers the fastener. The contained leg of the H penetrates the mesh and tissue. After ejection the fastener presumably returns to the equilibrium H shape with one leg below the tissue and one leg in contact with the mesh with the cross member penetrating the mesh and the tissue, similar to some plastic clothing tag attachments. Phillips depicts the installed device returning to the H shape but he fails to teach how to generate enough spring action from the device to overcome the high radial forces generated by the tissue.

A series of patents, U.S. Pat. Nos. 6,572,626, 6,551,333, 6,447,524, and 6,425,900 and patent applications 200200877170 and 20020068947 by Kuhns and Kodel, all assigned to Ethicon, describe super elastic, or shape metal fasteners and a delivery mechanism for them. The fasteners are stored in the delivery device in a smaller state and upon insertion into the mesh and tissue, transitions to a larger anchor shaped state. The Ethicon fastener is delivered by an elaborate multistage mechanism through a hollow needle that has penetrated the mesh and the tissue. The hollow needle is then retracted to leave the fastener to change shape to a more suitable configuration for holding the mesh in place.

The primary problem with these prior art fasteners is that the mesh is attached to body tissue in as many as 100 places for large ventral hernias. This results in a large quantity of metal remaining in the body as permanent implants, even though after the ingrowth phase the fasteners serve no useful purpose. Compounding this problem the distal ends of the fasteners are sharp pointed and thus pose a continued pain or nerve damage hazard.

One alternative to metallic fixation devices is bio-absorbable materials. These materials are degraded in the body by hydrolysis. After degradation the body metabolizes them as carbon dioxide and water. These materials require special attention to many design details that are much more demanding than their counterparts in metallic fixation devices such as applicator tool design, sterilization processes, and packaging. Metallic tacks or anchors provide structural strength that simplifies their insertion and since the materials, usually titanium or nickel-titanium alloys (shape metal), are chemical and radiation resistant and are very temperature tolerant many options are available to the designer. Not so for bio-absorbable materials.

The basic considerations of an effective mesh fixation applicator and absorbable anchor are the material strength, absorption time, the sterilization method, and packaging requirements, the ease of insertion of the anchor through the mesh and into the tissue, the ease of ejecting the anchor from the tool, the fixation strength of the anchor once implanted, the time required after insertion for the anchor to be degraded and metabolized by the body are all effected by the choice of anchor material, the geometry of the design, and the forming process.

Materials of appropriate strength are generally limited to synthetic materials. Currently, the U.S. FDA has cleared devices made from polyglycolide (PG), polylactide (PL), poly caprolactone, poly dioxanone, trimethylene carbonate, and some of their co-polymers for implant in the human body. These materials and their co-polymers exhibit a wide variation of properties. Flex modulus ranges from a few thousand to a few million PSI, tensile strength ranges from 1000 to 20,000 PSI, in vivo absorption times range from a few days to more than two years, glass transition temperatures range from 30-65 degrees centigrade, all with acceptable bio-responses. Unfortunately, however, the optimum values of each of these properties are not available in any one of these materials so that it is necessary to make performance tradeoffs.

Mechanical Properties

Most hernia mesh fixation devices are currently used in laparoscopic hernia repair. In general laparoscopic entry ports have been standardized to either 5 or 10 mm (nominal) diameter. In the case of prior art of metallic fixation devices 5 mm applicators are universally employed. Since it is not clear that the medical advantages of the use of absorbable anchors would totally out weigh the disadvantages of moving to a 10 mm applicator it must be assumed that absorbable anchors must also employ 5 mm applicators. Because of the lower strength of absorbable material this requirement imposes severe design constraints on both the applier and the anchor.

After successful insertion there are two ways for a fixation anchor to fail. It can fracture, separating the mesh holding feature from the tissue-snaring feature, or it can pull out of the tissue owing to inadequate tissue snaring. Increased forces are placed on the anchor during sudden elevations of intra-abdominal pressure (IAP) caused by straining, coughing or the Valsalva maneuver, a medical procedure whereby patients close their nose and mouth and forcibly exhale to test for certain heart conditions. The later can generate an IAP of up to 6.5 PSI. For nonporous mesh and a hernia area of 50 square centimeters, for example this increased IAP places 50.3 pounds of force on the anchors fixating the mesh. Typically 40 anchors would be used to secure the hernia mesh of 150 square centimeters so that each anchor would, at this elevated IAP, experience approximately a 1.26-pound tensile force on the mesh-retaining feature and the tissue-snare feature. The tensile strength between these two features and the tissue snare force must exceed this force generated by the increased IAP or else the mesh fixation can fail.

The strength and flexibility of the anchor material are of major importance in the design considerations of the applicator, particularly in the case of anchors formed from polymers. Ory, et al (U.S. Pat. No. 6,692,506) teaches the use of L Lactic Acid polymer. Ory discloses adequate fixation strengths but the applicator device required to insert his anchor is necessarily 10 mm in diameter thereby causing the procedure to be more invasive than necessary. Ory further discloses a hollow needle with a large outside diameter, through which the anchor is inserted, that forms a rather large hole in the mesh and tissue to supply adequate columnar strength for penetration of the anchor. Entry holes of this size can give rise to multiple small hernias know as Swiss cheese hernias.

Absorption Time

There are two forms of PL, one synthesized from the d optical isomer and the other from the l optical isomer. These are sometimes designated DPL and LPL. A polymer with 50-50 random mixture of L and D is herein designated DLPL.

High molecular weight homo and co-polymers of PG and PL exhibit absorption times ranging from 1 month to greater than 24 months. Homo crystalline PG and PL generally require greater than 6 months to absorb and thus are not optimum materials for hernia mesh fixation. Amorphous co-polymers of PG and PL, on the other hand, typically degrade in less than 6 months and are preferably used in the present invention. For high molecular weight co-polymers of PG and PL the actual absorption time is dependent on the molar ratio and the residual monomer content. For a given monomer residual the absorption time varies from about 1 month to about 5 months as the molar content of DLPL increases from 50 to 85 percent with PG decreasing from 50 to 15 percent. Co-polymers of DLPL and PG in the molar range of 50 to 85 percent of DLPL are preferred for this invention. The geometry of the anchor also effects the absorption time. Smaller high surface area devices absorb faster.

The time required for the human body to react to the foreign body of the mesh for tissue ingrowth into the mesh is typically 10 days. However, mesh migration and mesh contraction can occur for more than two months if not adequately stabilized. Since fixation anchors can impinge upon nerves and cause pain it is desirable for the anchors to be absorbed as soon as possible after the tissue ingrowth and after the mesh is secure against migration or contraction. For most absorbable materials there is a difference between the time for loss of fixation strength and mass loss. Fixation strength decreases quicker than anchor mass owing to some degree of crystalline structure in the polymer. For these reasons the preferred absorption time for the current invention is 3-5 months after implant.

Temperature Effects

Glass transition temperature (Tg) is the temperature above which a polymer becomes soft, can loose its shape, and upon re-cooling can shrink considerably. Both crystalline and amorphous polymers exhibit glass transitions in a temperature range that depends on the mobility of the molecules, which is effected by a number of factors such as molecular weight and the amount of residual monomers. Glass transition temperatures range from about 43 to 55 degrees centigrade (deg. C.) for co-polymers of PG and DLPL. Where as 100% PG has a Tg of 35-40 deg. C. and 100% PL exhibits a Tg from 50-60 deg. C. Since the core temperature of the body can reach 40 degrees C. the preferred Tg for the material comprising the current invention is greater than 40 deg. C. In addition hernia mesh anchors are often manufactured and shipped via surface transportation under uncontrolled, extreme heat conditions. Temperatures in commercial shipping compartments in the summer can exceed 60 degrees C. It is necessary then to provide thermal protection in the packaging so that the anchor temperature does not exceed its Tg.

Sterilization and Packaging

Bio-absorbable polymers degrade when exposed to high humidity and temperature. Autoclaving cannot be used, for example. Most ethylene oxide (ETO) sterilization processes employ steam and high temperatures (above Tg) to obtain reasonable "kill" times for the bio-burden commonly found on the device. High doses of gamma radiation or electron beam radiation (E Bream), both accepted methods of sterilization for many devices, could weaken the mechanical properties of PG, PL and their co-polymers. It is therefore necessary during the manufacturing process of the anchor and its applicator to maintain cleanliness to a high degree such that the bio-burden of the components is small enough so that pathogens are adequately eradicated with less severe forms of sterilization.

Radiation doses above 25 kilogray (kgy) are known to lessen the mechanical strength of bio-absorbable polymers whereas some pathogens are known to resist radiation doses below 10 kgy. It is therefore necessary, for the preferred embodiment of the present invention during manufacturing to keep the pathogen count below a certain threshold to insure the accepted regulatory standards are met for radiation levels between 10 and 25 kgy.

In a second embodiment of the present invention it is necessary during manufacturing to keep the pathogen count below a certain threshold to insure the accepted regulatory standards are obtained for sterilization using a non-steam, low temperature, ethylene oxide (ETO) process below Tg of the anchor polymer.

Anchors of the present invention must be carefully packaged to maintain adequate shelf life prior to use. Care must be taken to hermetically seal the device and to either vacuum pack, flood the package with a non-reactive dry gas prior to sealing, or to pack the device with a desiccant to absorb any water vapor since hydrolysis breaks down the backbone of the co-polymers.

ETO sterilization requires the gas to contact the device to be sterilized. Devices that are not humidity sensitive can be packaged in a breathable packaging material so that ETO can diffuse in, and after sterilization, diffuse out so that the device can be sterilized without unsealing the packaging. For the alternate embodiment of the present invention the device must be hermetically sealed after sterilization with ETO. Since gamma radiation and electron beam radiation sterilization can be accomplished through hermetically sealed packaging without disturbing the seal, either of these two sterilization processes is employed for the preferred embodiment of the present invention.

Ory, et al (U.S. Pat. No. 6,692,506), Criscuolo, et al (US application 20040092937), Phillips (U.S. Pat. Nos. 5,203,864 and 5,290,297), Kayan (U.S. application 20040204723), and Shipp (U.S. application Ser. Nos. 10/709,297 and 10/905,020) have suggested the use of bio-absorbable materials for use as hernia mesh fixation devices to solve the problems associated with the permanency of metal implants. Ory, preferably, suggests forming the fixation device from LPL but the absorption time for LPL can exceed two years, much longer than optimum for hernia fixation devices since the lessening of pain depends on mass loss of the device. While Phillips and Kayan advocate the use of bio-absorbable material to form the anchor neither teach any details or methods for effectuating such a device. Criscuolo suggests the use of PG and PL with an absorption time of 2-3 weeks but does not disclose a method of forming the device that results in such an absorption time. In any respect, migration and contraction of the mesh has been documented to occur up to 8 weeks after implant. Loss of fixation after 2 to 3 weeks could well lead to hernia recurrence.

Hernia mesh such as PTFE based mesh manufactured by W. L. Gore is difficult to penetrate since the material is tough, non macro-porous, and relative inelastic. Attempts to penetrate these types of meshes with a puncture type applicator result in the mesh indenting into the tissue to a significant depth prior to penetration, especially for soft tissue. This indentation sometimes allows the tissue penetrator means, often a hollow needle, to penetrate through the abdomen wall and into the surgeon's hand, thus exposing the surgeon to potential hepatitis and AIDS viruses. The anchor of the present invention is equipped with screw threads that easily penetrate tough, non macro-porous, and relative inelastic mesh with a minimum of indentation. Once the threads are screwed through the mesh the underlying tissue is pull toward the mesh by the threads rather than push away from the mesh as is the case with puncture type devices.

Details of the method of manufacturing the improved anchor are herein provided.

What is needed then is an absorbable mesh fixation anchor and a method of forming an absorbable mesh fixation anchor that exhibits a known absorption time and that exhibits the mechanical properties adequate for the desired fixation strength and the required implant forces.

What is also needed is a method of packaging an absorbable mesh fixation device and the delivery device that minimizes the effects of high ambient shipping temperatures and humidity.

What is also needed is a method of sterilization of an absorbable mesh fixation anchor and its delivery device that has minimal effect on their physical properties, particularly the anchor.

What is further needed then is an absorbable mesh fixation anchor of improved geometry that easily penetrates tough, non macro-porous, and relatively inelastic mesh with minimal indentation to minimize the possibility of the anchor breaching the abdominal wall.

SUMMARY OF THE INVENTION

A method of producing and deploying a bio-absorbable hernia mesh fixation anchor exhibiting an in vivo absorption time between 1.5 and 13 months and its method of use is disclosed. A method of sterilization and a method of packaging the anchor to retain the critical physical properties of the anchor prior to implantation are also disclosed. The hernia mesh fixation device of the present invention is, preferably, injection molded using any of a variety of mole fractions of d, l-lactide and glycolide co-polymers, depending upon the desired absorption time, and mechanical properties. Preferably the mole ratio is 75-25 percent d, l lactide to glycolide yielding an absorption time after implant of 4-5 months and a glass transition temperature of 49 Deg. C. The modulus of elasticity of the preferred embodiment is 192,000 PSI and the tensile strength is 7200 PSI after injection molding at 150 Deg. C.

The anchor of the present invention comprises a head with a threaded portion and a slotted portion, a threaded tissue-snaring section formed on a truncated body section that, upon rotation, easily penetrates tough, non macro-porous, and relative inelastic mesh and pulls underlying tissue toward the head of the anchor, firmly anchoring the mesh to the tissue and thus avoiding excessive indentation of the abdominal wall during deployment.

The anchor deliver device, or applier, of the present invention has a longitudinal axis, a handle, an actuator engaged with a rotator, an anchor retainer, an anchor advancer, a force reactor, and an anchor ejector.

Sterilization standards by the U.S. FDA allow radiation doses less than 25 kgy provided the bio-burden is below 1000 colony forming units (CFU). The components of the delivery device and the anchors of the present invention are manufactured and assembled under clean room conditions such the bio-burden is well below 1000 CFUs. This allows gamma and E Beam sterilization with doses below the damage threshold of the preferred co-polymers of DLPL and PG, 25 kgy. Mechanical properties of the injected molded anchor of the present invention have been retested after dosing with 25 kgy E Beam. The same values of flex modulus and tensile strength were measured before and after dosing. Gamma or E Beam is the preferred sterilization process, however, an alternate embodiment comprises sterilization employing ethylene oxide without the use of steam and dosed at a temperature below the glass transition temperature.

For the preferred embodiment of the present invention the delivery device loaded with anchors is first sealed into a vacuum formed tray with a breathable Tyvek (a registered trademark of DuPont) lid. This tray is then further hermetically sealed into a foil pouch. The foil pouch is then placed inside an insulated shipping container. The insulation is adequate to assure that the temperature of the anchor remains below 30 deg. C. after exposure to severe heat conditions sometimes experienced during shipping. Gamma or E Beam sterilization is accomplished by radiation through the shipping container.

In an alternate embodiment the sealed vacuum formed tray is placed into the hermetically sealed foil pouch after ETO sterilization. The ETO will penetrate the breathable lid. After the ETO process the device is sealed into the foil pouch and the pouch is placed into the thermally insulated container described above for shipping.

DETAILED DESCRIPTION

Figure 1:
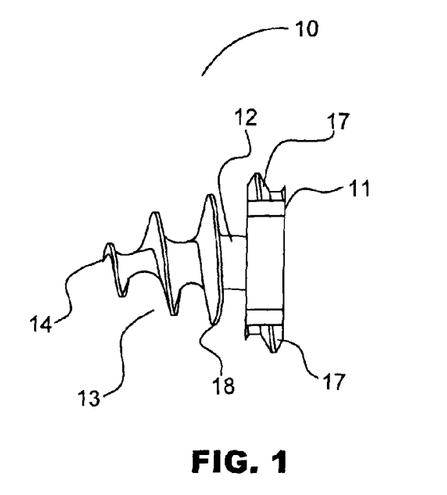
FIG. 1 is a side view of the anchor according to the present invention.
Figure 2:
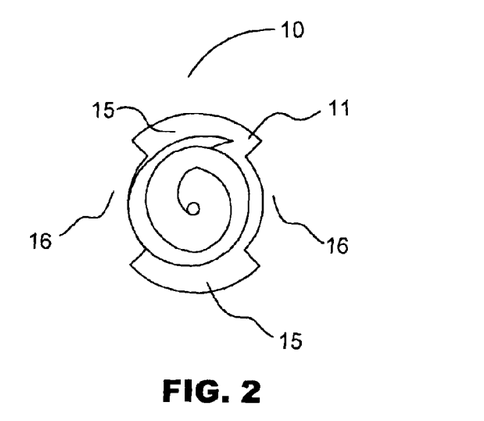
FIG. 2 is the distal end view of the anchor according to the present invention.
Figure 3:
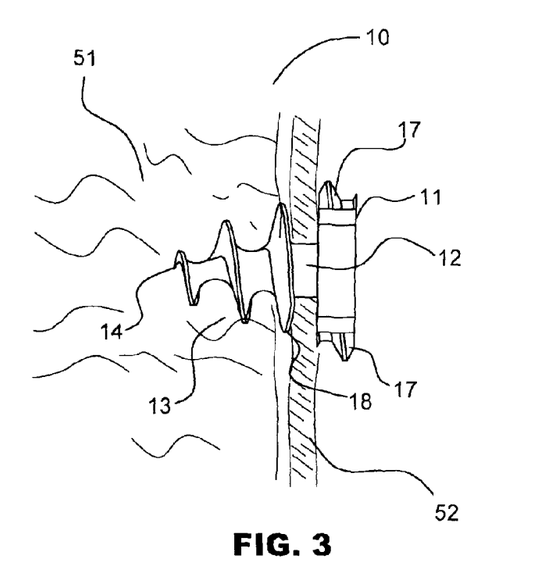
FIG. 3 depicts the anchor fixating mesh to tissue.

Turning now to FIGS. 1, 2 and 3, depictions of the anchor of the current invention, generally designated as 10. Anchor 10 comprises three sections, head section 11, mesh retention section 12, and threaded tissue-snaring section 13. Head section 11 comprises two opposing threaded sections 15 with head threads 17 and two opposing open or slotted sections 16. The distal surface of head section 11 is formed onto the proximal end of mesh retention section 12.

Figure 1A:
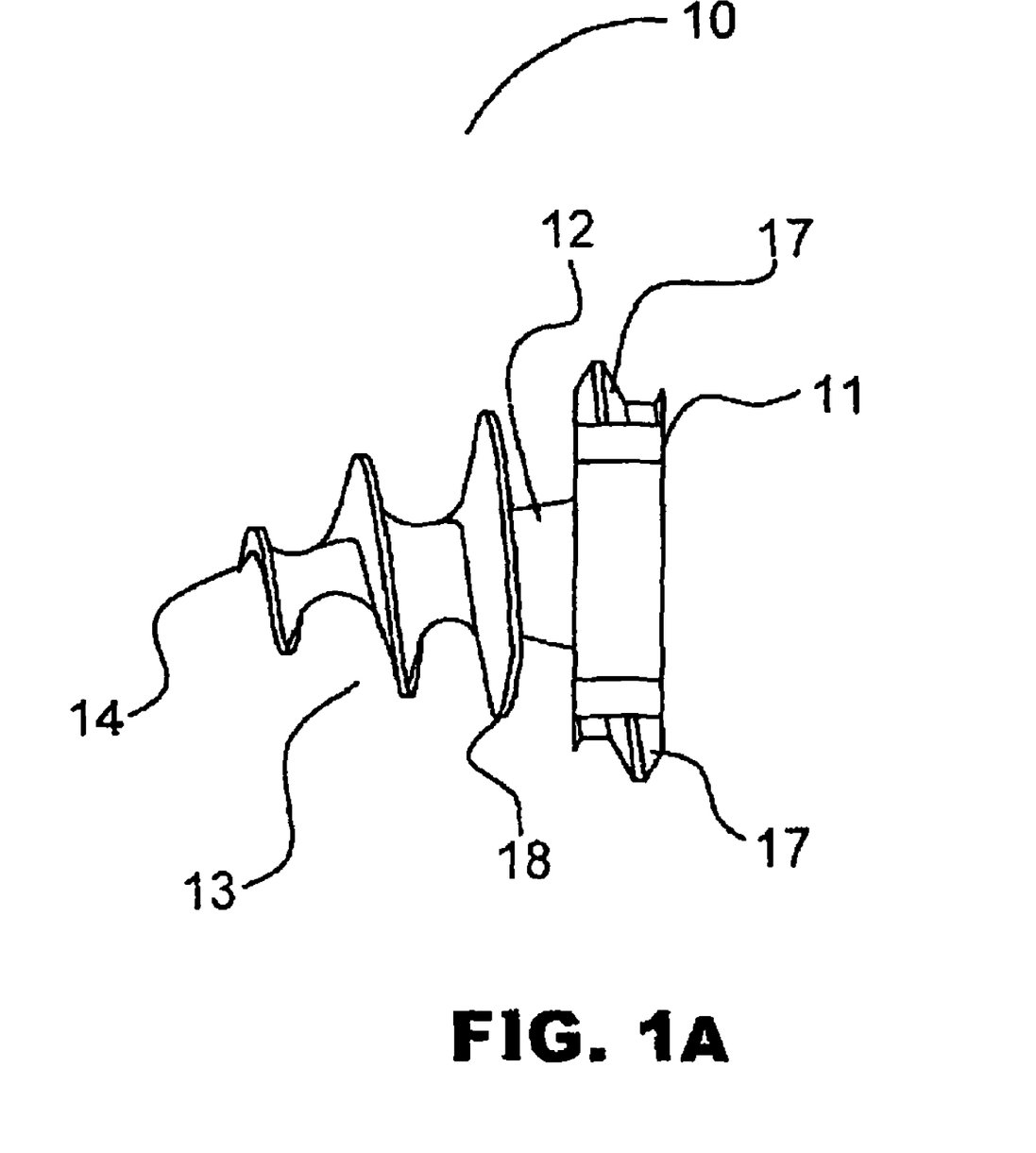
FIG. 1A is a side view of an anchor according to another embodiment of the present invention.

Mesh retention section 12 may, alternately, be tapered or right-cylinder shaped or may be omitted, which would allow the proximal end of threaded tissue-snaring section 13 to abut the distal end of head section 11. Unlike the embodiment of anchor 10 with no mesh retention section 12, either the conical or cylindrical configuration mesh retention section 12 locks mesh 52 on anchor 10 when mesh 52 is screwed past the proximal-most tissue-snaring thread 18 since there is no thread located in mesh retention section 12 that would allow mesh 52 to be unscrewed from anchor 10. Mesh retention section 12 is generally cylindrical or conical shaped (see FIG. 1A) with a dimension transverse to its longitudinal axis that is smaller than the transverse dimension of head 11 and the transverse dimension of proximal most tissue-snaring thread 18.

With continued reference to FIGS. 1, 2 and 3, the slotted section 16 of the head section 11 defines opposing rotational force transmitting surfaces. Additionally, as seen in FIGS. 1, 2 and 3, the two opposing threaded sections 15 provide opposing longitudinal stabilizing structures. The rotational force transmitting surfaces of each of the rotational force transmitting recesses 16 extends substantially parallel to the longitudinal axis. The longitudinal stabilizing structures defined by each threaded section 15 includes opposing surfaces that extend longitudinally along the outer circumference of the head section 11 and radially outward along a perimeter of the outer circumference of the head section 11. Each of the opposing surfaces of the threaded sections 15 are configured to provide reaction forces in both, a longitudinal direction and a radial direction, the radial direction being perpendicular to the longitudinal axis.

Figure 4:
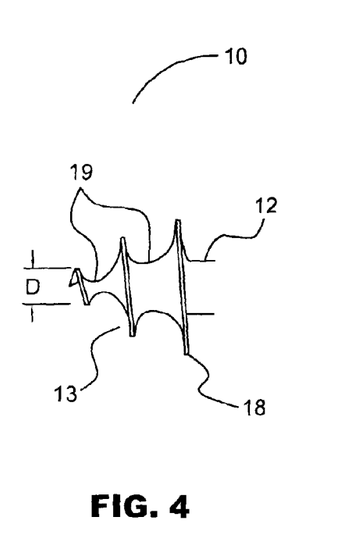
FIG. 4 depicts the shape of the tissue penetrating threads of the anchor.

Threaded tissue-snaring section 13 comprises helical threads formed onto a tapered truncated body section 19. Distal point 14 is the terminus of the distal most tissue-snaring thread. FIG. 4 is an angled view of the threaded tissue-snaring section 13 of the preferred embodiment. Body section 19 is tapered and thus becomes smaller toward the distal end of threaded tissue-snaring section 13 and terminates, or truncates, distally prior to reaching an apex. The taper can take the form of a linear taper, a convex, or a concave taper. A concave taper is preferable in that it, for a given length, yields the minimum diameter body section 19 upon truncation, preferably less than 0.01 inches. The dimension D shown in FIG. 4 is the transverse dimension of the distal most thread in the threaded tissue-snaring section 13. D should be as large as design constraints will allow, preferably greater than 0.040 inches. A small truncated body diameter and a large value of D minimizes tissue indentation. The tissue-snaring threads terminate at distal tip 14, which is distal of the truncation point of body section 19. This geometry allows for ease of mesh penetration and minimizes indentation of the mesh into soft tissue as compared to a non-truncated body with tapered threads. For a given force applied to mesh 52 by the surgeon exerting a distal force on applier 20 the larger is the dimension D the less the pressure to cause indentation of tissue 51 and mesh 52.

Figure 5:
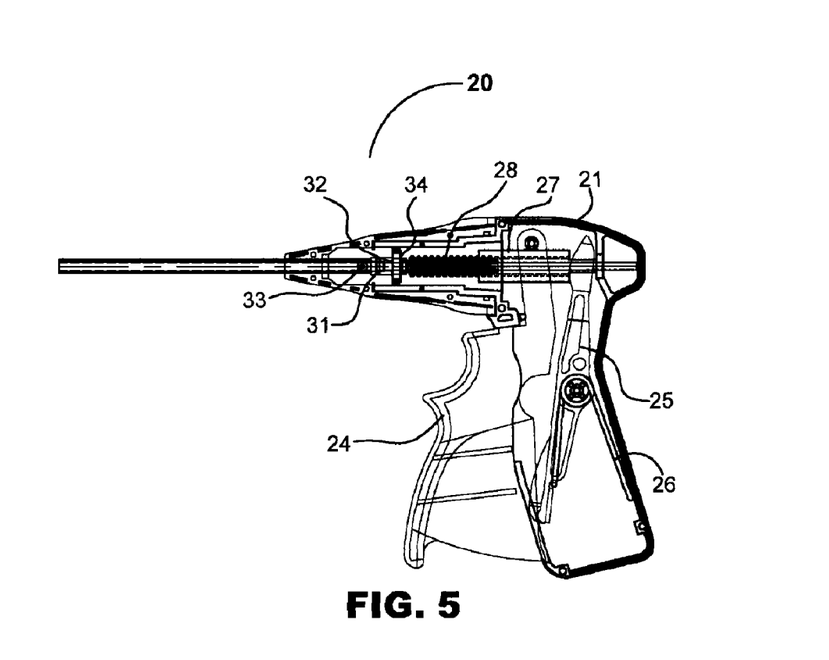
FIG. 5 is a cutaway view of the proximal end of the applier according to the present invention.
Figure 6:
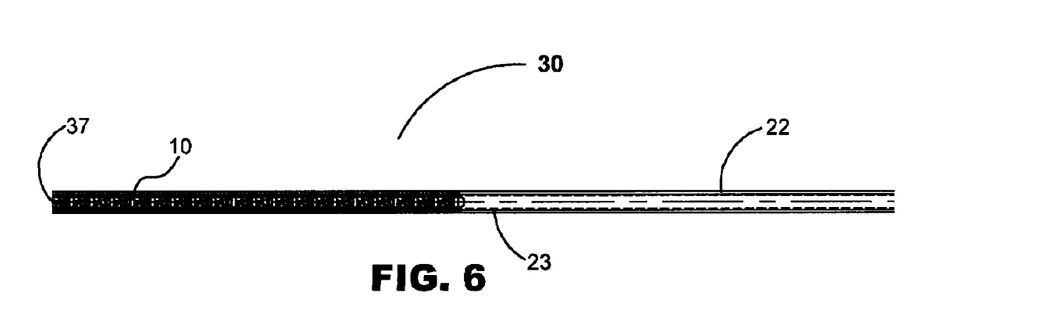
FIG. 6 is a cutaway view of the distal end of the applier according to the present invention.
Figure 7:
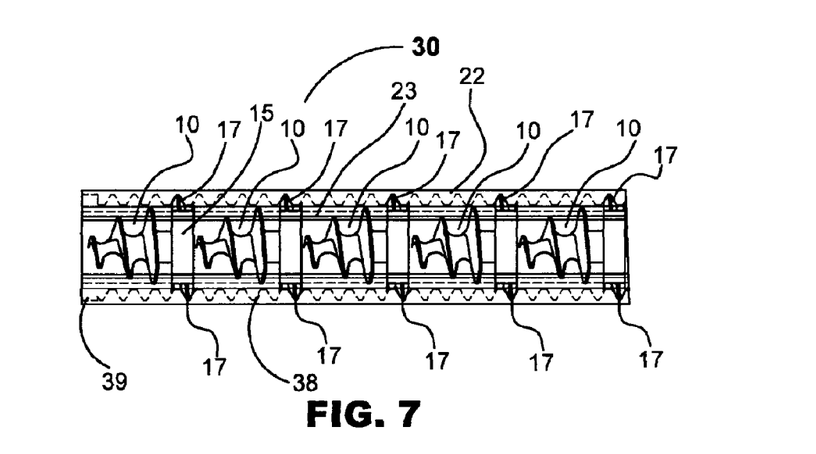
FIG. 7 is an enlargement of a cutaway view of the distal end of the applier according to the present invention.

Turning now to FIGS. 5, 6, and 7 depicting the delivery device, or applier, for mesh anchor 10, generally designated as 20. FIG. 5 is a cutaway view of the proximal or handle end of applier 20. The proximal end of applier 20 comprises handle 21, outer tube 22, inner tube 23, trigger 24, actuator 25, return spring 26, helix nut 27, helix 28, clutch pin 31, clutch 32 clutch engager 34, and outer tube pins 33. FIG. 6 depicts the distal end 30 of applier 20 with twenty anchors 10 loaded ready for use. FIG. 7 is cutaway view of an enlargement of the distal end 30 of applier 20 depicting the distal most five anchors 10. Head threads 17 of anchors 10 engage internal screw threads 38 in outer tube 22. The distal end of inner tube 23 is slotted to accept multiple anchors 10 leaving two tines and two slots, not shown because of the cutaway. The two tines engage slots 15 in anchors 10 and head threads 17 extend through the inner tube slots 16 to engage outer tube threads 38. Rotation of inner tube 23 about its longitudinal axis rotates anchors 10 and advances them distally owing to head threads 17 engagement with outer tube threads 38. In the preferred embodiment anchors 10 are not in forced engagement with each other to avoid damage to distal tip 14 of anchors 10.

In a preferred embodiment there are twenty-four tube threads 38 per inch, the overall length of anchor 10 is 0.203 inches, with five full turns of inner tube 23 advancing anchors 10 0.208 inches. The distal end of outer tube 22 comprises counter bored 39 that preferably has a depth of 0.030 inches, which allows distal most anchor 10 to release from outer tube threads 38 in the last three quarters of a turn of a five turn actuation sequence in the application and ejection process, as will be detailed below.

Five embodiments of anchor 10 are described herein comprising four different molar ratios of DLPL and PG. The resins of the co-polymers in each case were prepared using well-known techniques of polymerization of cyclic dimmers. The molar percentages (M) of DLPL and PG were measured along with the residual monomer percentage (RM). After polymerization the resins were thoroughly dried. Anchor 10 was then injection molded in a standard micro-molding machine at 150 Deg. C. The transition glass temperature (Tg), the absorption time at 37 Deg. C. (to 20% of the original mass) (AT), the tensile strength (TS) and Young's modulus (YM) were then measured. Anchor 10 was then subjected to 25 kgy E Beam radiation and the tensile strength and Young's modulus re-measured. Standard techniques, well known by those skilled in the art, were employed in the measurements of each of the parameters. The results are shown below:

Case I

| Parameter | M, DLPL, % | M, PG, % | RM, % | Tg, Deg. C. | AT, Months | TS, PSI | YN, PSI |
|---|---|---|---|---|---|---|---|
| | 100 | 0 | 2.1 | 49.4 | 13 | 6100 | 206,000 |

Case II

| Parameter | M, DLPL, % | M, PG, % | RM, % | Tg, Deg. C. | AT, Months | TS, PSI | YN, PSI |
|---|---|---|---|---|---|---|---|
| | 85 | 15 | 2.1 | 49.7 | 5.8 | 7900 | 198,000 |

Case III

| Parameter | M, DLPL, % | M, PG, % | RM, % | Tg, Deg. C. | AT, Months | TS, PSI | YN, PSI |
|---|---|---|---|---|---|---|---|
| | 75 | 25 | 1.6 | 49.1 | 4.3 | 7200 | 192,000 |

Case IV

| Parameter | M, DLPL, % | M, PG, % | RM, % | Tg, Deg. C. | AT, Months | TS, PSI | YN, PSI |
|---|---|---|---|---|---|---|---|
| | 65 | 35 | 1.9 | 47.2 | 3.2 | 74000 | 190,000 |

Case V

| Parameter | M, DLPL, % | M, PG, % | RM, % | Tg, Deg. C. | AT, Months | TS, PSI | YN, PSI |
|---|---|---|---|---|---|---|---|
| | 52 | 48 | 1.2 | 46.7 | 1.5 | 8100 | 188,000 |

In each case retesting the tensile strength and Young's modulus after subjecting the anchor 10 to 25 kgy E Beam radiation yielded results statistically indistinguishable from the values in the tables above.

To design an appropriate insulated shipping container the historical average daily temperatures over a "hot weather route" from Florida to Arizona were obtained from the Average Daily Temperature Archive available through The University of Dayton (Source Data from the National Climatic Data Center). Heat flux data were determined from the historical data resulting in an insulation requirement of 2.5 inches of Cellofoam (a registered trademark of Cellofoam of North America, Inc.) with a thermal R-value of 3.86 per inch of thickness. Anchors 10 were then shipped over the route packed in the insulated container and the internal temperature of a un-air conditioned cargo space of a roadway common carrier was measured during a five-day trip from Jacksonville Fla. to Phoenix Ariz. from Sep. 9 till Sep. 14, 2004. The internal temperatures of the cargo space, Tc, and the internal temperature of the insulated container, Ti, containing anchors 10 were recorded every 30 minutes. The minimum and maximum temperatures in the cargo space and the insulated container are shown below:

| | Day 1 | Day 2 | Day 3 | Day 4 | Day 5 |
|---|---|---|---|---|---|
| Maximum Tc Deg. C. | 37 | 34 | 29 | 48 | 50 |
| Minimum Tc Deg. C. | 24 | 18 | 15 | 27 | 27 |
| Maximum Ti Temperature, Deg. C. | 27 | 27 | 26 | 27 | 27 |
| Minimum Ti Temperature, Deg. C. | 24 | 26 | 21 | 24 | 24 |

Thus it is seen from the data above that the insulated shipping container is adequate for maintaining anchor 10 temperatures well below the glass transition temperature of 49 Deg. C. of the preferred co-polymer, 75/25 DLPL/PG, Case III above.

The preferred embodiment for the current invention is an injection molded anchor as depicted in FIG. 1 comprising 75% DLPL, 25% PG, sterilized with radiation, either gamma or E Beam, at 25 kgy and packaged first in a hermetically sealed pack and an insulated shipping container.

Applier Loading and Operation

Multiple anchors 10 are loaded onto the tines of inner tube 23 head to tail with tips 14 pointed distally. Anchors 10 are rotationally orientated such that the tines of inner tube 23 engage head slots 16. The proximal end of the loaded inner tube assembly is inserted into the distal end of outer tube 22 until proximal-most anchor 10 encounters outer tube threads 38. The inner tube assembly is then rotated until the distal end of inner tube 23 is flush with or slightly recessed into outer tube 22. In this position the proximal end of inner tube 23 is proximal of the proximal end of outer tube 22. Near the proximal end of inner tube 23 a drill through hole perpendicular to the longitudinal axis is located to accept clutch pin 31 for securing clutch 32 to inner tube 23. The inner and outer tube and clutch assembly is then affixed into handle 21 with outer tube pins 33 (one from each side) which allows for inner tube 23 to rotate inside outer tube 22.

The loaded applier 20 is placed into a surgical field, usually through a 5 mm trocar, and the distal end of applier 20 is held firmly against mesh 52, which covers tissue 51. Outer tube threads 38 act as a force reactor to counter the distal force, generated by the screw-in process of the threaded tissue-snaring section 13, so that anchors 10 are unable to move proximally. Outer tube threads 38 engaging head threads 17 also restrain anchors 10 from falling out of the distal end of applier 20 under the influence of gravity, for example.

Trigger 24 is then squeezed rotating actuator 25 against helix nut 27. Helix nut 27 and helix 28 are design according to well-known art such that the force applied to helix nut 27 causes helix nut 27 to move distally and rotate helix 28 in a right-hand manner when helix nut 27 and helix 28 are threaded in a left hand manner. The primary design consideration is the coefficient of static friction (COSF) between helix nut 27 and helix 28 for a given helix thread pitch. According to well-known art there exists a critical value of COSF for a given pitch above which the system is self-locking and below which helix nut 27 linear movement causes helix 28 to rotate. In the preferred embodiment the system comprises a left hand double helix with a pitch of 0.100 inches, lead of 0.200 inches and COSF less than 0.2 and preferably less than 0.15. One inch distal movement of helix nut 27 causes helix 28 and clutch engager 34 to make five full revolutions. Clutch 32 is designed such that as helix 28 and hence clutch engager 34 rotate in a right-hand sense inner tube 23 rotates five full turns in a right-hand sense. As explained above rotation of inner tube 23 rotates anchors 10. Tip 14 of distal most-anchor 10 engages and penetrates mesh 52 and threaded tissue-snaring section 13 screws into and draws tissue 51 and mesh 52 together. During the last three quarters of a rotation of the five revolutions head threads 17 of distal most anchor 10 enter into counter bore 39. Removal of the distal end 30 of applier 20 from mesh 52 releases distal-most anchor 10 and ejects it from applier 20. Mesh 52 is thus affixed to tissue 51. After the anchor screw-in process is complete trigger 24 is released, reset spring 26 returns actuator 25 to its start, or home, position. This returns helix nut 37 proximally since it is attached to actuator 25. As helix nut 37 returns proximal helix 28 and clutch engager 34 rotates in the left-hand sense. Clutch 31 is detached from the rotation owing to the clutch design, thus inner tube 23 does not rotate during the reset process leaving the stack of anchors 10 forward in the same position as before, less distal-most anchor 10. Applier 20 is fully reset and ready for the deployment of the next anchor 10.

From the foregoing, it will be appreciated that the absorbable anchor of the present invention functions to securely fasten tough, non macro-porous, and relative inelastic mesh to tissue. The anchor of the present invention will disintegrate after the body has secured the mesh against migration and contraction. The absorbable anchor of the present invention can be sterilized so that mechanical properties are maintained and it can be shipped under severe temperature conditions with insulated packaging so that the glass transition temperature is not exceeded. It will also be appreciated that the absorbable anchor of the present invention may be utilized in a number of applications such as hernia repair, bladder neck suspension, and implant drug delivery systems.

While several particular forms of the invention have been illustrated and described, it will be apparent by those skilled in the art that other modifications are within the scope and spirit of the present disclosure.

What is claimed is:

1. A mesh anchor for penetrating tissue and fixating mesh having a longitudinal axis comprising:

a head section with a distal surface and a proximal surface perpendicular to the longitudinal axis, the head section defining an outer circumference having opposing rotational force transmitting recesses and opposing longitudinal stabilizing structures, each of the rotational force transmitting recesses defining at least one surface that extends substantially parallel to the longitudinal axis, each of the longitudinal stabilizing structures defining opposing surfaces that extend longitudinally along the outer circumference of the head section and radially outward along a perimeter of the outer circumference of the head section, each of the opposing surfaces of the stabilizing structures configured to provide reaction forces in both a longitudinal direction and a radial direction, the radial direction being perpendicular to the longitudinal axis, the head section including threads extending from the opposing longitudinal stabilizing structures, a truncated body section having a proximal end and a distal end and a length, the proximal end of which is attached to the distal surface of the head, wherein the body section defines a surface, and threads extending from the surface of the body section, the threads having a root diameter and a substantially constant thread angle along an entire length thereof to define substantially parallel threads, and wherein the threads extend distally beyond the truncated body section.

2. The mesh anchor according to claim 1 wherein the anchor comprises a bio-absorbable polymer, either a homo polymer of either polylactide or polyglycolide or co-polymer of polylactide and polyglycolide.

3. The mesh anchor according to claim 1 wherein the anchor polymer exhibits a young's modulus in the range of 150,000 to 2,000,000 PSI.

4. The mesh anchor according to claim 1 wherein the anchor exhibits a tensile strength in the range of 5,000 to 10,000 PSI.

5. The mesh anchor according to claim 1 wherein the anchor polymer exhibits an absorption time in vivo between 1.5 and 14 months.

6. The mesh anchor according to claim 1 wherein the anchor exhibits a glass transition temperature in the range of 40 to 60 degrees centigrade.

7. The mesh anchor according to claim 1 wherein the thread to root diameter ratio is between 1.25 and 5.

* * * * *